United States Patent [19]
Hirai et al.

[11] Patent Number: 5,902,877
[45] Date of Patent: May 11, 1999

[54] ADSORBENT OF INTERLEUKINS, PROCESS FOR REMOVING THE SAME, AND ADSORBER FOR THE SAME

[75] Inventors: Fumiyasu Hirai, Amagasaki; Nobutaka Tani, Osaka; Takamune Yasuda; Takashi Asahi, both of Kobe; Yuji Okubo; Osamu Odawara, both of Takasago; Michio Nomura, Kakogawa, all of Japan

[73] Assignee: Kanegafuchi Kagaku Kogyo Kabushiki Kaisha, Osaka, Japan

[21] Appl. No.: 08/646,266

[22] PCT Filed: Sep. 18, 1995

[86] PCT No.: PCT/JP95/01859

§ 371 Date: May 20, 1996

§ 102(e) Date: May 20, 1996

[87] PCT Pub. No.: WO96/09115

PCT Pub. Date: Mar. 28, 1996

[30] Foreign Application Priority Data

Sep. 21, 1994 [JP] Japan .................................. 6-226906
Feb. 28, 1995 [JP] Japan .................................. 7-040882

[51] Int. Cl.⁶ ...................................................... A23J 1/00
[52] U.S. Cl. ........................................... 530/412; 530/351
[58] Field of Search ....................................... 530/351, 412

[56] References Cited

U.S. PATENT DOCUMENTS

| | | |
|---|---|---|
| 4,472,303 | 9/1984 | Tanimara et al. . |
| 4,723,000 | 2/1988 | Georgiades et al. ..................... 530/416 |
| 5,338,834 | 8/1994 | Williams .................................. 530/351 |

FOREIGN PATENT DOCUMENTS

| | | |
|---|---|---|
| 0 190 606 A2 | 8/1986 | European Pat. Off. . |
| 0 366 532 A1 | 5/1990 | European Pat. Off. . |
| 0 426 857 A1 | 5/1991 | European Pat. Off. . |
| 61-106519 | 5/1986 | Japan . |
| 3-16639 | 1/1991 | Japan . |
| 5-18625 | 3/1993 | Japan . |
| 6-256399 | 9/1994 | Japan . |

OTHER PUBLICATIONS

Patent Abstracts of Japan; vol. 17, No. 582 (C–1123) & JP 05 170799 A (Toray Ind.), Jul. 9, 1993.
Yabuki et al., "Container Containing Anionic Adsorbent", CAPLUS # 1991:542398, Jan. 24, 1991.
Nakatani et al., "Adsorbent & Methods for Removing Chemokines" CAPLUS # 1997:671643, Sep. 24, 1997.
Sakurai et al., "Purification of IL–8" CAPLUS # 1993:579163, Jul. 9, 1993.
Freifelder, *"Physical Biochemistry"* W.H. Freeman & Co. pp. 248–255, 1982.

*Primary Examiner*—Cecilia J. Tsang
*Assistant Examiner*—Patrick R. Delaney
*Attorney, Agent, or Firm*—Armstrong, Westerman, Hattori, McLeland & Naughton

[57] ABSTRACT

The present invention relates to an adsorbent being capable of efficiently adsorbing and removing interleukins in a body fluid and to a method for adsorbing and removing, if necessary, and recovering interleukins in a body fluid with the above-mentioned adsorbent. According to the present invention, there are provided an adsorbent of interleukins which comprises a water-insoluble carrier having an anionic functional group, a method for adsorbing, removing and recovering interleukins using the same and an adsorber using the same.

10 Claims, 2 Drawing Sheets

ADSORBENT OF INTERLEUKINS, PROCESS FOR REMOVING THE SAME, AND ADSORBER FOR THE SAME

TECHNICAL FIELD

The present invention relates to an adsorbent of interleukins, a process for removing the same, and an adsorber of the same. More particularly, the present invention relates to the adsorbent which adsorbs at least one interleukin selected from the group consisting of interleukin-8 (hereinafter referred to as IL-8), interleukin-1β (hereinafter referred to as IL-1β), interleukin-6 (hereinafter referred to as IL-6) and interleukin-2 (hereinafter referred to as IL-2) and to the process for removing and the adsorber by means of the above-mentioned adsorbent.

BACKGROUND ARTS

A cytokine is a greatly important proteinous substance as a biophylactic factor which closely relates to various kinds of antigen-specific, non-specific immune inflammatory responses. The existance thereof is necessary and indispensable for maintaining biological homeostasis and the cytokine is produced excessively in a disease with inflammation, relating to the formation and the prolongation of pathology of the disease.

"IL-8" is one kind of cytokine purified as a monocyte-derived neutrophil chemotactic factor (MDNCF) by Matsushima et al. and gene thereof has also been cloned in 1987. IL-8 is a neutrophile-activation migration regulatory factor produced by various kinds of cells.

It is known that IL-8 acts on a neutrophil to enhance functions for inhibiting growth of *Candida albicans* and Mycobacterium which the neutrophil has, and it is anticipated that IL-8 has an effect as an immunoactivation agent (Nipponigakukan, Cytokine—From Foundation to The Latest Information—, 1991, pages 65–72). Therefore, there has been desired a method for efficiently purifying IL-8 in a large amount from a body fluid or a culture medium.

On the other hand, the continuous administration of IL-8 in a large amount is remarkably harm to tissues, and causes the destruction of tissues of adult respiratory distress syndrome in an alveolus and the destruction of tissues with the infiltration of lymphocytes in a large amount in an arthrosis. Experimentally, it is shown that IL-8 relates essentially to the infiltration of neutrophils in dermatitis derived from lipopolysaccharide (LPS) and during reperfusion after ischemia. This has been proved by the fact that the destruction of tissues accompanied by the above-mentioned infiltration of lymphocytes or neutrophils can be inhibited almost completely by administrating a neutralizing antibody against IL-8. Further, an abnormally higher concentration of IL-8 has been detected in an inflammatory site or in peripheral blood of patients with diseases such as rheumatoid arthritis (RA), gouty arthritis, psoriasis, contact dermatitis, septicemia, idiopathic fibroid lung, adult respiratory distress syndrome, inflammatory bowel disease, immune angiitis, glomerular nephritis, urinary tract infection, cardiac infarction, asthma, respiratory tract infection, perinatal infectious disease and rejection in organ transplantation, than that of a normal human (refer to Menekiyakuri, 12, No. 1, pages 15–21 (1994)). And, it is considered that IL-8 relates to these diseases. At present, however, an efficient method to inhibit the function of IL-8 in these diseases has not been established.

Then, "IL-1β" is an inflammatory cytokine which is produced mainly by a monocyte and/or a macrophage with stimulation by a foreign matter such as bacteria, and in 1984, the gene of human has been cloned by Auron et al.

As seen from the fact that IL-1β has been discovered as an endogenious pyrogen (EP), a leukocytic endogenious mediator (LEM), a lymphocyte activation factor (LAF), a B cell-activating factor (BAF) and the like until the standardized name of interleukin 1 (IL-1) was determined as the same substance at The 2nd International Lymphokine Workshop in 1979, the bioactivity thereof is shown in various functions.

Though IL-1β, which is a main mediator of an inflammation, plays an important role in various kinds of reactions including homeostasis of a living body in the ordinary state, it has been clear that IL-1β induces the destruction of tissues or the formation and/or deterioration of pathology in the inflammatory diseases when IL-1β is produced excessively or conteniously for a long term in some mechanism (Biomedica, 9, 1993, pages 703–707). The relation of IL-1β to each of pathological conditions such as toxic syndrome including septicemia, RA, Lyme disease, osteoporosis, Kawasaki disease, gout, glomerulonephritis, ectatic cardiomyopathy, endometritis, premature labor, granuloma, acute myelogenous leukemia, Alzheimer disease, Down syndrome, hepatic fibrosis, hepatoma, further, alcoholic hepatitis is strongly suggested (Nipponigakukan, Cytokine—From Foundation to The Latest Information—, 1991, pages 13–20 and pages 177–187), and a method of specific inhibition of IL-1β is hoped for and researched enthusiastically.

Though, as the representative, an antiIL-1β antibody, an antiIL-1β receptor antibody, an IL-1 receptor antagonist (IL-1ra) and the like were developed (Igakunoayumi, 167, 1993, pages 432–435) and a part thereof was subjected to a clinical testing of septicemia as an objective disease, each did not give an effect to be expected and has not yet been put into practice.

Also, "IL-6" was originally isolated as a differentiating factor of a B cell and the structure of the gene thereof was determined by Hirano, Kishimoto et al. in 1986. It is recognized that IL-6 has a function as a main mediator of inflammation, for instance, to work as a proliferating factor of myelocytoma, and to derive an acute phase protein in liver.

It is shown by the production of a transgenic mouse that the abnormal production of IL-6 brings about a polyclonal activation of a B cell and causes plasmocytoma Also, in general, it has been observed that IL-6 in blood shows a high value in many acute inflammatory diseases or bacterial infection, virus infection, scald, myocardial infarction and the like. An example has been reported wherein IL-6 level was actually raised at the time of infestation such as scald or surgical operation and, in a cerebrospinal fluid of a patient with acute bacterial meningitis (by pneumococcus, staphylococcus, Listeria), up to 500 ng/ml of IL-6 was detected. On the other hand, IL-6 was detected in local inflammatory tissues or a general body of chronic hepatitis. In an autoimmune disease such as RA, Castleman disease or atrial myxoma, there is the abnormal production of IL-6 and it is considered that this triggers the production of proteins in hypergammaglobulinemia. In addition, it is suggested that the involvement of IL-6 to the diseases such as cancer of the uterine cervix, AIDS, alcoholic hepatitis, multiple myeloma, Lennert T lymphoma, mesangial proliferative nephritis, renal cytoma psoriasis and septicemia (Nipponigakukan, Cytokine—Foundation to The Latest Information—, 1991, pages 177–187). For the time being, however, an effective method for inhibiting specifically the function of IL-6 in these diseases has not yet been established.

Further, "IL-2" is a glycoprotein having a molecular weight of approximately 15 kDa which was conventionally called a T cell growth factor (TCGF) and is a cytokine of which gene was cloned by Taniguchi et al. in 1983. It is intended that the application of IL-2 as a remedy for cancer according to single therapy or local adoptive immunotherapy since IL-2 has a proliferation facilitating activity against T cell.

On the other hand, the opinion was obtained, suggesting that IL-2 continuously produced at a locality (in this case, at pancreas) is one of potent pathogenesis of autoimmune diabetes mellitus from an experiment using a transgenic mouse (Heath W. R., Allison J. et al.: Nature, 359, page 547, 1992). Also, it was also reported that the administration of IL-2 caused the development of both systemic lupus erythematosus (SLE) and RA (Chazerain P., Meyer O., Kahn M.-F., Ann. Intern. Med., 116, page 427, 1992 and Wandl U. B., Nagel-Hiemke M., May D. et al.: Clin. Immunol. Immunopathol., 65, page 70, 1992). Further, the possibility is suggested that IL-2 together with TNF-α relates closely to the pathologic conditions in the septic shock (Endo S., Inada K., Inoue Y. et al.: Circulatory Shock, 38, page 264, 1992). For the time being, however, an effective method for inhibiting the function of IL-2 in these diseases has not yet been established.

By considering the above-mentioned situation, the inventors of the present invention researched with respect to a method for adsorbing and removing IL-8, IL-1β, IL-6 and/or IL-2 as a pathogenic substance from a body fluid of a patient and, if necessary, a method for recovering the same. As the result of repeating whole-hertedly investigation, the inventors discovered that a water-insoluble carrier having an anionic functional group, when in contact with a body fluid, adsorbs strongly IL-8, IL-1β, IL-6 and IL-2 in the body fluid and proceeded the investigation to reach the completion of the present invention.

An object of the present invention is to selectively adsorb and remove IL-8, IL-1β, IL-6 and/or IL-2 from a body fluid, particularly, blood, plasma and serum and, if necessary, to recover the same.

DISCLOSURE OF THE INVENTION

Namely, the present invention relates to an adsorbent comprising a water-insoluble carrier having an anionic functional group for adsorbing at least one interleukin selected from the group consisting of interleukin-8, interleukin-1β, interleukin-6 and interleukin-2 and to a method for adsorbing and removing at least one interleukin selected from the group consisting of interleukin-8, interleukin-1β, interleukin-6 and interleukin-2, characterized in that the adsorbent is brought into contact with a body fluid. And, the present invention relates to a method for recovering at least one interleukin selected from the group consisting of interleukin-8, interleukin-1β, interleukin-6 and interleukin-2, which comprises a step to adsorb an interleukin by bringing a water-insoluble carrier having an anionic functional group into contact with a liquid which may contain at least one interleukin selected from the group consisting of interleukin-8, interleukin-1β, interleukin-6 and interleukin-2 and a step to elute the adsorbed interleukin. Then, the present invention relates to an adsorber for adsorbing at least one interleukin selected from the group consisting of interleukin-8, interleukin-1β, interleukin-6 and interleukin-2 wherein a vessel which has an inlet and an outlet for a fluid and is equipped with a means to prevent the adsorbent from flowing to the outside of the vessel, is charged with the adsorbent.

In the above-mentioned adsorbent, preferably the anionic functional group comprises at least one kind of group selected from the group consisting of sulfuric ester group, sulfonic acid group, carboxyl group and phosphoric ester group, and is originated from at least one compound selected from the group consisting of sulfuric acid, dextran sulfate and polystylene sulfonate and/or is a polyanionic functional group having plural anionic functional groups within the above-mentioned functional group.

Also, in the above-mentioned adsorbent, preferably the water-insoluble carrier is hydrophilic, porous, and/or there exists an end functional group represented by —OH in the water-insoluble carrier.

In the present invention, the body fluid means blood, plasma, serum, ascites, lymph, synovia and a fraction component obtained therefrom and another liquid component derived from a living body.

"IL-8" is a protein having a molecular weight of approximately 8000 and has been reported to exist as a monomer or dimer (Science, 264, pages 90 to 92).

"IL-1β" is a protein having a molecular weight of approximately 17,500 which comprises 153 amino acids and of which isoelectric point is 7 to 8. IL-8 is produced from a monocyte or a macrophage and has various biological activities such as derivation of proliferation or differentiation of an immunocompetent cell, an endogenious pyrogen activity, and derivation of an inflammatory reaction such as synthesis of acute phase inflammatory protein in liver. And, "IL-6" is a glycoprotein having a molecular weight of approximately 21,000 to approximately 28,000 which is produced from a non-lymphoid cell as well as from a lymphoid cell.

"IL-2" is a glycoprotein having a molecular weight of approximately 15,000 produced from a T cell. It is known that IL-2 facilitates proliferation, differentiation or activation of a function against a T cell, a B cell, a NK cell, a monocyte, a macrophage and the like.

The water-insoluble carrier used in the present invention is solid at ordinary temperature under ordinary pressure and the solid surface may be coated with a water-insoluble material.

The form of the water-insoluble carrier of the present invention is not particularly limited. For example, the form is one of a particle, a board, a film, a fiber or the like. In case of the form of a fiber, the fiber may be hollow. In the present invention, the water-insoluble carrier is may be used with which a column is charged.

In case where the adsorbent is used with which a column is charged, it is preferable that blood can pass through it. Namely, it is preferable that openings enough for cells contained in blood to pass through them can be made. For example, if the adsorbent is in the form of a particle and it is intended that IL-8 is adsorbed, it is preferable that the average particle size is 5 to 1000 μm. Preferably, the average particle size is 25 to 1000 μm and most preferably, the average particle size is 50 to 300 μm. If the average particle size is not more than 5 μm, a body fluid cannot stably pass through the adsorbent at a high flow rate for a long period of time. If not less than 1000 μm, the adsorption efficiency is decreased. In case of a particle, it is more preferable that the distribution of the particle size is narrow.

And, if the adsorbent is in the form of a fiber and is hollow, it is preferable that the inner diameter is not less than 5 μm. If it is intended to adsorb IL-8, the inner diameter is preferably 20 to 1000 μm and most preferably 30 to 300 μm.

In case in the form of a fiber of which inside is not empty, it is preferable that the diameter is not less than 1 μm. And, if it is intended to adsorb IL-8, the diameter is preferably 2 to 500 μm and most preferably 5 to 200 μm. It is preferable that the surface of the water-insoluble carrier is smooth. And, it is not preferable that the surface is rough since non-specific adsorption is increased and selectivity is decreased.

The anionic functional group in the present invention can be any one containing a functional group which is negatively charged at a pH of around neutral. The representative examples of such functional group are, for instance, carboxyl group, sulfonic acid group, sulfuric ester group, silanol group, phosphoric ester group, phenolic hydroxyl group and the like. Among them, in order to adsorb IL-1β, IL-6 and/or IL-2, sulfonic acid group and sulfuric ester group are preferable, but the anionic functional group is not limited thereto. Also, these functional groups can be used alone or by combining at least 2 kinds of the groups. In order to adsorb IL-8, as the preferable anionic functional group, sulfuric ester group, sulfonic acid group, carboxyl group and phosphoric ester group can be exemplified.

Also, the anionic functional group in the present invention may be a monoanionic functional group having one anionic functional group per molecule or may be a polyanionic functional group having plural monoanionic functional groups. The polyanionic functional group is preferable since the polyanionic functional group has a high affinity to IL-8, IL-1β, IL-6 and IL-2 and is easy to introduce many monoanionic functional groups into a unit amount of the water-insoluble carrier. Among them, the polyanionic functionl group having a molecular weight of not less than 1000 is more preferable in such a point of affinity to IL-8, IL-1β, IL-6 and IL-2 and in such point that many monoanionic functional groups can be introduced into the carrier. The monoanionic functional group which the polyanionic functional group has may be one kind or may be two or more kinds of the group.

In order to adsorb IL-8, it is preferable that 100 nmol to 10 mmol of the anionic functional group of the present invention is contained per unit volume (1 ml) of the water-insoluble carrier. Preferably, the contained amount is 1 to 200 μmol and most preferably is 5 to 100 μmol. If less than 100 nmol, the effect of the anionic functional group is small and if more than 10 mmol, non-specific adsorption of substances other than the above-mentioned interleukins.

The representative examples of the compound to introduce the polyanionic functional group are, for instance, synthetic polyanionic compounds such as poly(acrylic acid), poly(vinyl sulfuric acid), poly(vinyl sulfonic acid), poly(vinyl phosphoric acid), poly(styrenesulfonic acid), poly(styrenephosphoric acid), poly(glutamic acid), poly(aspartic acid), poly(methacrylic acid), poly(phosphoric acid) and styrene-maleic acid copolymer, and polysaccharides having an anionic functional group such as heparin, dextran sulfate, chondroitin, chondroitin sulfate and phosphomannan, but the compound is not limited to them. Also, the representative examples of the compound to introduce the monoanionic functional group are, for instance, the compound such as sulfuric acid, but the compound is not limited thereto. Preferably, the anionic functional group is originated from at least one compound selected from the group consisting of sulfuric acid, dextran sulfate and poly(styrene sulfonic acid).

Further, the anionic functional group in the present invention comprises at least one kind of the functional group selected from the group consisting of the above-mentioned monoanionic functional group and/or polyanionic functional group, and it may comprise at least 2 kinds thereof. Also, the monoanionic functional group and polyanionic functional group can be contained together.

As the water-insoluble carrier having an anionic functional group which is the adsorbent of the present invention, a compound having an anionic functional group itself can be employed. Also, a polymer obtained by polymerizing monomers having anionic functional groups or a water-insoluble carrier obtained by introducing an anionic functional group thereinto can be employed.

And, to avoid non-specific adsorption of blood cell components during blood passes through the adsorbent, for example, the adsorbent may be coated with an adequate macromolecule such as a polymer of hydroxyethylmethacrylate. Also, this coating may be carried out to prevent finely divided particles from generating from the adsorbent.

Examples of the water-insoluble carrier used in the present invention are, for instance, inorganic carriers such as a glass bead, a silica gel and alumina, organic carriers comprising a synthetic macromolecule such as crosslinked poly(vinyl alcohol), crosslinked polyacrylate, crosslinked polyacrylamide or crosslinked polystyrene, or a polysaccharide such as crystalline cellulose, crosslinked cellulose, crosslinked agarose or crosslinked dextran, and further complex carriers such as organic-organic carrier and organic-inorganic carrier which can be obtained by a combination thereof, and the like. Among them, a hydrophilic carrier is preferable since non-specific adsorption is relatively little and adsorption selectivity of IL-8, IL-1β, IL-6 and IL-2 is excellent. Here, the hydrophilic carrier means a carrier having a contact angle of at most 60° with water. The contact angle is of a compound constituting the carrier which is made to be in the form of a flat panel. As such a carrier, there can be exemplified carriers comprising a polysaccharide such as cellulose, chitosan, Sephalose or dextran, poly(vinyl alcohol), saponified ethylene-vinyl acetate copolymer, polyacrylamide, poly(acrylic acid), poly(methacrylic acid), poly(methyl methacrylate), poly(acrylic acid-grafted polyethylene), poly(acrylamide-grafted polyethylene), glass, or the like, as the representative example. Among them, a carrier wherein —OH group exists is superior in such points of adsorption performance and selectivity. Among them, a porous cellulose gel is the most preferable one for a carrier used in the present invention because of such superior points as the followings:

① the carrier of a porous cellulose gel is hardly destroyed or generates finely devided particles by the operation of agitation and the like because of a relatively high mechanical strength and toughness. The carrier is neither compacted nor clogged up when a column is charged therewith and a body fluid is passed through the column at a high flow rate. Further, the pore structure hardly changes by high-pressure steam sterilization.

② The carrier is hydrophilic since the gel is constituted by cellulose. There exist many hydroxyl groups available for bonding a ligand, and non-specific adsorption is little.

③ If volume of porosity is enlarged, comparable adsorption volume can be obtained to a soft gel since the strength is relatively high.

④ Safty is high compared to a sythetic macromolecular gel and the like. The carrier is not limited to these carriers mentioned above. Also, each of the above-mentioned carriers can be used alone or can be used by mixing optionally 2 or more kinds thereof.

The adsorbent in the present invention can adsorb IL-8, IL-1β, IL-6 and/or IL-2 only at the outer surface. The characteristics required for the water-insoluble carriers to adsorb more IL-8, IL-1β, IL-6 and/or IL-2 is that the adsorbent has many pores of an adequate size, namely the adsorbent is porous. The molecular weight of IL-8, which is an object to be adsorbed of the adsorbent of the present invention, has a molecular weight of approximately 8000, IL-1β has a molecular weight of approximately 17,500, IL-6 has a molecular weight of approximately 21,000 to approximately 28,000, and IL-2 has a molecular weight of approximately 15,000. Therefore, to adsorb effeciently these proteins, it is preferable that IL-8, IL-1β, IL-6 and IL-2 can enter the pores with somewhat high probability and enter of other proteins do not occur, as little as possible.

To measure the pore size, a method of mercury porosimetry is used most frequently. In case of the porous water-insoluble carrier used in the present invention, however, the method of mercury porosimetry cannot be applied so often and it is suitable that a molecular weight of exclusion limit is used as a measure of the pore size of the gel. The molecular weight of exclusion limit means the minimum molecular weight of the molecule which cannot enter a pore (i.e. the molecule is excluded) in a gel permeation chromatograph (written by Hiroyuki Hatano and Toshihiko Hanai, Experimental High Performance Liquid Chromatography, Kagaku Dojin). The molecular weight of exclusion limit for a globular protein, dextran, polyethylene glycol or the like has been quite studied in general, and in case of the carriers used in the present invention it is suitable to employ a value obtained using the globular protein.

The molecular weight of IL-1β is approximately 17,500 and the molecular weight of IL-6 is approximately 21,000 to approximately 28,000. Therefore, in order to adsorb IL-1β and/or IL-6, when the carrier having a molecular weight of exclusion limit of lower than $3 \times 10^4$ is used, the amount of adsorbing and removing IL-1β and/or IL-6 is low and the practicability is decreased. Therefore, the preferable molecular weight of exclusion limit of the carrier used for IL-1β and/or IL-6 is not less than $3 \times 10^4$ and, further, it is preferable that the molecular weight of exclusion limit is not less than $5 \times 10^4$.

With respect to the adsorption of IL-2, since the molecular weight of IL-2 is approximately 15,000, when the carrier having a molecular weight of exclusion limit of lower than $1 \times 10^4$ is used, the adsorbed and removed amount of IL-2 is low and the practicability is decreased. Therefore, the preferable molecular weight of exclusion limit of the carrier used for IL-2 is not less than $1 \times 10^4$ and, further, it is preferable that the molecular weight of exclusion limit is not less than $2 \times 10^4$. As far as plasma or serum is used as a body fluid, there is no upper limitation in the molecular weight of exclusion limit.

Further, in case where blood is used as a body fluid, there is a tendency that the percentage of adhesion of blood platelet is increased when the molecular weight of exclusion limit is over $5 \times 10^6$. In case where the adsorbent of the present invention is used in a hemocatharsis system of direct hemo-perfusion (DHP)-type, sufficient performance is not necessarily exhibited. Therefore, it is preferable that the molecular weight of exclusion limit is not more than $5 \times 10^6$. Namely, the molecular weight of exclusion limit in case where blood is used as a body fluid is $3 \times 10^4$ to $5 \times 10^6$, further preferably $5 \times 10^4$ to $5 \times 10^6$.

On the other hand, for the adsorption of IL-8, the molecular weight of exclusion limit is $1 \times 10^4$ to $1 \times 10^6$, preferably $3 \times 10^4$ to $5 \times 10^5$, and more preferably $5 \times 10^4$ to $2 \times 10^5$. This value is basically constant even if the carrier is in the form of a particle, a plate or a fiber.

Then, the porous structure of the carrier is explained. By considering an adsorption performance per unit volume of the adsorbent, all-porosity is more preferable than surface-porosity. And, it is preferable that the volume of porosity is not less than 20% and specific surface area is not less than $3 \text{ m}^2/\text{g}$. Also, with respect to the form of the carrier, the form of a particle, a fiber, hollw or the like can be selected optionally.

Further, it is advantageous for an immobilization reaction of ligands if a functional group used for the immobilization reaction of ligands exists on the surface of the carrier. The representative examples of the functional group are, for instance, hydroxyl group, amino group, aldehyde group, carboxyl group, thiol group, silanol group, amido group, epoxy group, a halogen group, succinylimide group, acid anhydride group and the like.

Then, as the carrier used in the present invention, each of a hard carrier and a soft carrier can be used. To use as the adsorbent for extracoroporeal circulation treatment, in case where a column is charged with the carrier and a fluid passes therethrough, and the like, it is important that the column does not clog up. For that reason, sufficient mechanical strength is required. Therefore, it is more preferable that the carrier used in the present invention is hard one. The term "hard carrier" used in the present invention means, for instance, in case that a gel is a granulated gel as shown in Reference Example described below, the carrier wherein a relationship between pressure loss ΔP and flow rate is linear relationship up to 0.3 kg/cm² of pressure loss when a cylindrical column is charged uniformly with the gel and aqueous fluid is passed through the column.

The adsorbent of the present invention is characterized in that the adsorbent comprises the water-insoluble carrier having an anionic functional group. To obtain such a water-insoluble carrier having an anionic functional group, there are various methods to introduce an anionic functional group into the water-insoluble carrier, and the anionic functional group can be introduced by any methods. As the representative introducing method, there can be exemplified, (1) a method for forming an adsorbent by means of polymerization using as a monomer or a crosslinking agent a compound having an anionic functional group or a functional group which can easily convert to the anionic functional group, (2) a method for immobilizing a compound having an anionic functional group onto the water-insoluble carriers, and (3) a method for immobilizing a compound having an anionic functional group onto the water-insoluble carrier by reacting directly the compound having an anionic functional group with the water-insoluble carrier.

As the representative example of the monomer or crosslinking agent having an anionic functional group or a functional group which can easily convert to the anionic functional group used in the method (1), there can be exemplified acrylic acid and an ester thereof, methacrylic acid and an ester thereof, styrenesulfonic acid and the like. The monomer or crosslinking agent is, however, not limited to these compounds.

As the method (2), namely the method for immobilizing a compound having an anionic functional group onto the water-insoluble carrier, there are a method by means of physical adsorption, a method by means of ionic bond, a method for immobilizing by means of covalent bond and the like, and any methods can be used. Since it is important that the compound having an anionic functional group is not released for preservation and safety of the adsorbent, the method by means of covalent bond capable of a strong immobilizing is preferable.

In case where the compound having an anionic functional group is immobilized by means of covalent bond, it is preferable that the compound having an anionic functional group is a polyfunctional compound having a functional group available for the immobilization other than the anionic functional group. In case where the compound having a polyanionic functional group is immobilized, the immobilization may be carried out using a part of the anionic functional group.

As the representative example of the functional group available for immobilization, there can be exemplified amino group, amide group, carboxyl group, acid anhydride group, succinylimide group, hydroxyl group, thiol group, aldehyde group, a halogen group, epoxy group, silanol group and the like. The functional group available for immobilization is not limited to these compounds.

For example, in case where a compound having sulfuric ester group is immobilized onto the water-insoluble carrier by means of covalent bond, as the representative example of a compound having sulfuric ester group, there can be exemplified, sulfuric ester compound derived from a compound having hydroxyl group such as alcohol, saccharide or glycol. Among them, partially sulfuric ester compound derived from a polyalcohol and, particularly, sulfuric ester compound derived from a polysaccharide are more preferable since they have both of sulfuric ester group and a functional group necessary for the immobilization and can be easily immobilized onto the water-insoluble carrier.

Then, as the method of (3), namely the method for introducing an anionic functional group by immobilization of a compound having an anionic functional group onto the water-insoluble carrier by reacting directly the compound having an anionic functional group with the water-insoluble carrier, there can be exemplified a method for introducing sulfuric ester group into the water-insoluble carrier having hydroxyl group. In this case, sulfuric ester group can be directly introduced by reacting the water-insoluble carrier having hydroxyl group with a reagent such as chlorosulfonic acid or concentrated sulfuric acid.

Further to these three kinds of methods, there is (4) a method for obtaining the water-insoluble carrier having a polyanionic functional group by graft-polymerizing a compound having an anionic functional group or a functional group which can easily convert to the anionic functional group as a monomer on the water-insoluble carrier.

Then, there are various methods, as the method for adsorbing and removing the interleukin selected from the group consisting of IL-8, IL-1β, IL-6 and IL-2 in a body fluid by bringing the adsorbent comprising the water-insoluble carrier having an anionic functional group into contact with a body fluid. As the representative method, there is a batch-type method wherein a body fluid is taken and stored in a bag or the like, and the adsorbent is mixed therewith to adsorb and remove the interleukin selected from the group consisting of IL-8, IL-1β, IL-6 and IL-2, and then the adsorbent is filtered off to obtain the body fluid from which the interleukin selected from the group consisting of IL-8, IL-1β, IL-6 and IL-2 is removed. And, there is a continuous-type method wherein a vessel having an inlet and an outlet for a fluid is equipped with a filter through which a body fluid can pass and the adsorbent cannot pass, and the vessel is charged with the adsorbent, and the body fluid is flowed under ordinary pressure or under high pressure. There are also other methods. Any methods can be used. With respect to the latter method, however, the operation thereof is simple, and IL-8, IL-1β, IL-6 and IL-2 can be removed efficiently on-line from a body fluid of a patient by incorporating the latter method into extracorporeal circulation cycle. Therefore, the adsorbent of the present invention is suitable for this method. Both methods can be combined and used together.

Recovering of IL-8 adsorbed on the adsorbent can be carried out by treating the adsorbent on which IL-8 is adsorbed with, for example, an aqueous solution having a high concentration of salts, e.g., phosphate-buffered saline (PBS) containing sodium chloride having a concentration of 0.5 M and by eluting the adsorbed IL-8. A buffer solution with concentration gradient of salts can also be used. Besides, IL-1β, IL-2 and/or IL-6 can also be recovered in the same way.

The above-mentioned removal and recovery can be carried out by means of the batch-type method, the continuous-type method or the combination of these two methods. In case of the continuous-type method, it is also easy to recover IL-8 from the adsorbent by a simple operation. These methods are effective, for example, in case where IL-8 is recovered from a culture medium containing IL-8 by culturing a microorganism into which the gene of IL-8 is incorporated or in case where IL-8 is recovered from blood.

BRIEF DESCRIPTIONS OF THE DRAWINGS

BEST MODE FOR CARRYING OUT THE INVENTION

Figure 1:
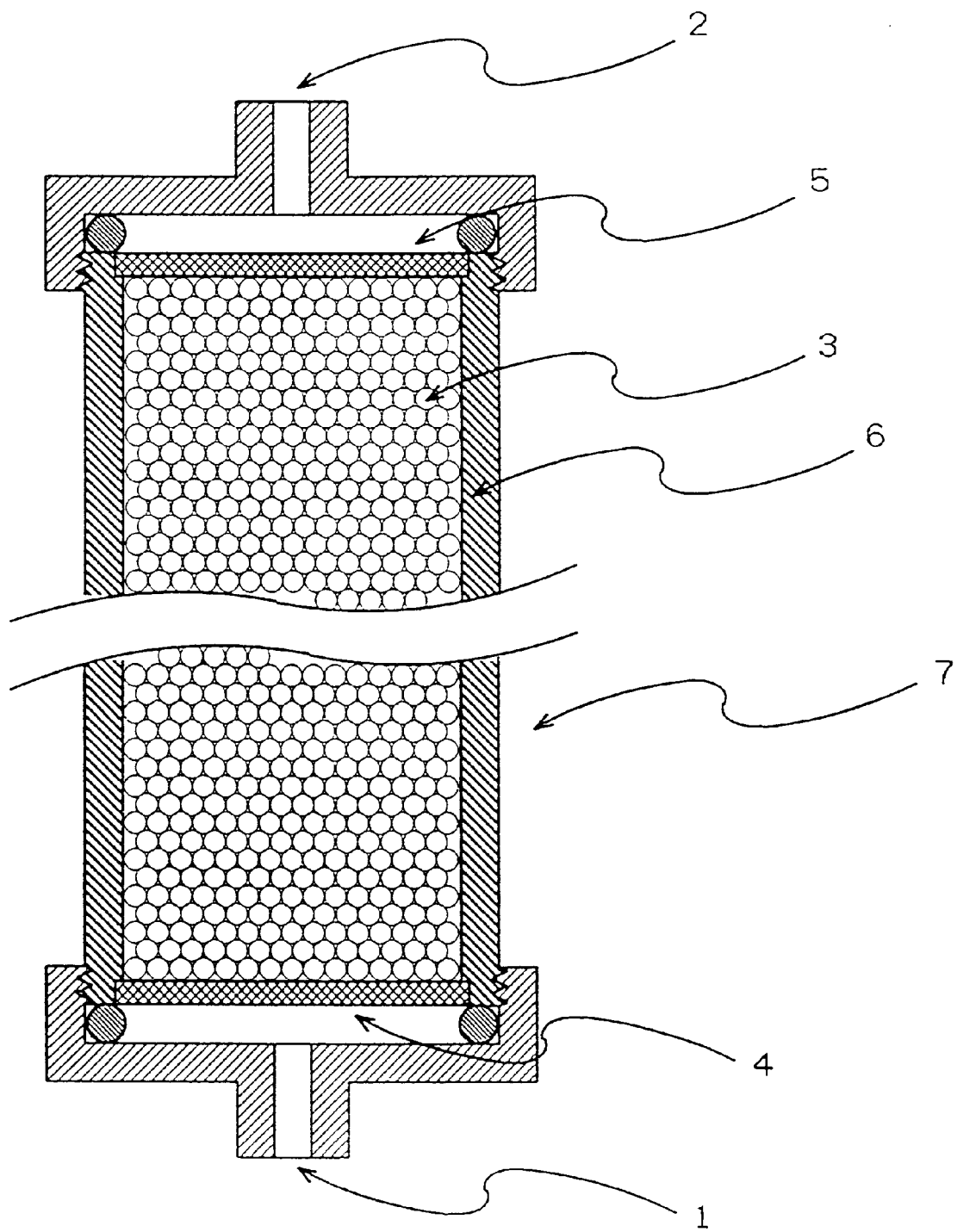
FIG. 1 is a schematic cross section of one example of the adsorber of IL-8, IL-1β, IL-6 and/or IL-2 of the present invention.

Then, the adsorber of IL-1β of the present invention using the adsorbent of IL-1β is explained based on FIG. 1 which is a cross section of one example thereof. Besides, the adsorber of IL-8, IL-1β, IL-6 and/or IL-2 is the same as the above-mentioned adsorber of IL-1β.

In the figure, 1 is an inlet of a body fluid, 2 is an outlet of a body fluid, 3 is the adsorbent of IL-1β (IL-8, IL-6, IL-1β and/or IL-2) of the present invention, 4 and 5 are means to prevent the adsorbent of IL-1β (IL-8, IL-6, IL-1β and/or IL-2) from flowing out through which a body fluid and components contained in the body fluid can pass but the adsorbent cannot pass, 6 is a column, 7 is an adsorber. The form and quality of material of the vessel of the above-mentioned adsorber are not limited. As the concrete example, however, for example, there can be given a cylindrical vessel having volume of approximately 150 to approximately 400 ml and a diameter of approximately 4 to approximately 10 cm.

The present invention is explained in detail by means of the following Examples and, however, the present invention is not limited to the following Examples.

REFERENCE EXAMPLE

Each of cylindrical columns of glass (inner diameter 9 mm, length of column 150 mm) equipped with filters having a pore size of 15 μm on both ends, was charged uniformly with an agarose gel (Biogel A-5m made by BIO-RAD, particle size: 50 to 100 meshes), a vinyl-type polymer gel (TOYOPEARL HW-65 made by TOSOH Corporation, particle size: 50 to 100 μm) or a cellulose gel (CELLULOFINE GC 700-m made by CHISSO CORPORATION, particle size: 45 to 105 μm). And, the relationship between flow rate and pressure loss ΔP was determined by passing water through the columns with a peristaltic pump. The results are shown in FIG. 2.

Figure 2:
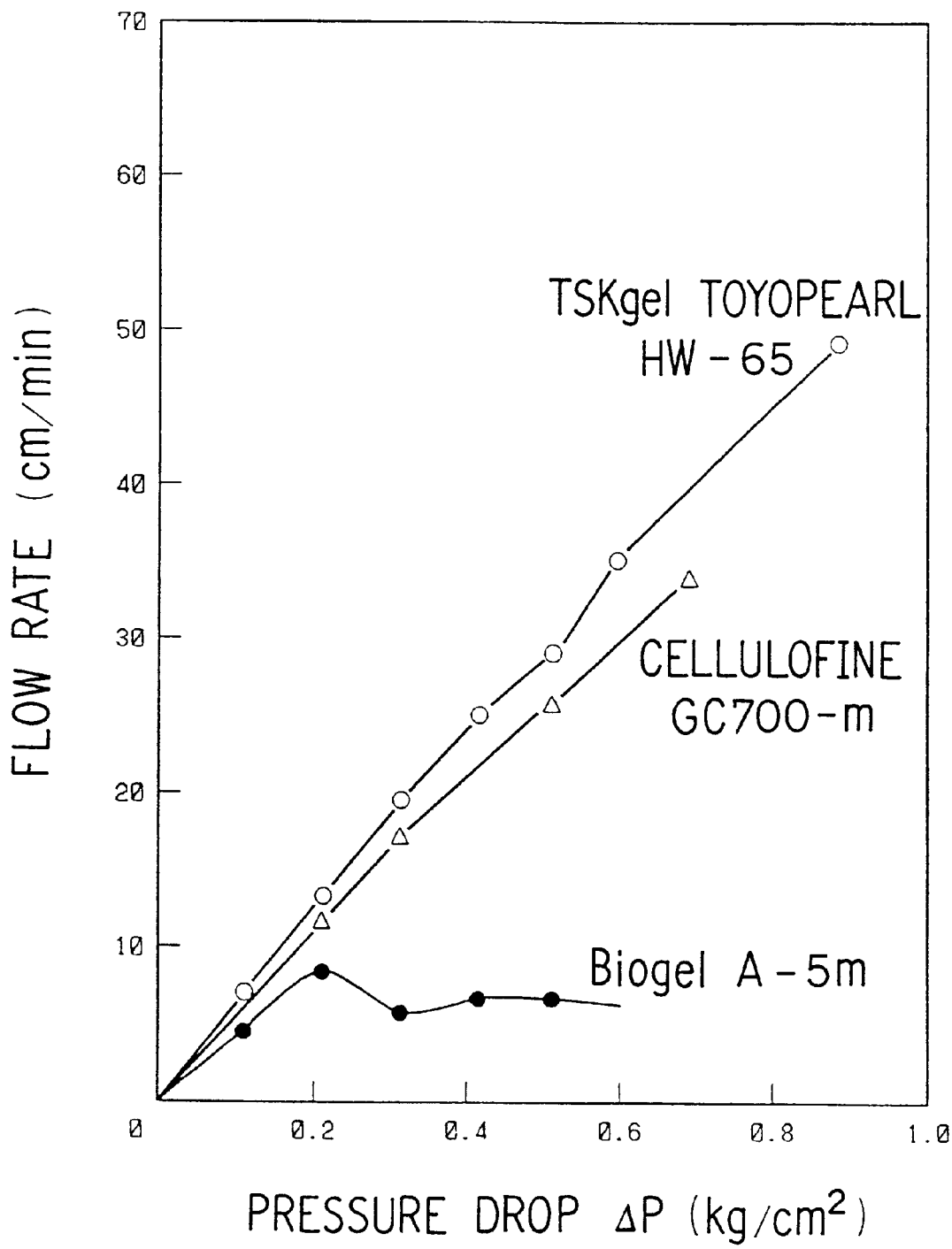
FIG. 2 is a graph showing the result of investigating the relationship between the flow rate and pressure loss by using 3 kinds of gels.

As shown in FIG. 2, it is found that each flow rate in cases of TOYOPEARL HW-65 and CELLULOFINE GC-700m increases almost in proportion to the increase of pressure. On the other hand, it is found that Biogel A-5m causes the compaction and flow rate does not increase if the pressure is increased. In the present invention, as the former, the gel of which the relationship between pressure loss ΔP and flow rate is in linear relationship up to 0.3 kg/cm$^2$ is defined as a hard gel.

EXAMPLE 1

Preparation of an adsorbent: To 10 ml of CELLULOFINE GC 200-m (molecular weight of exclusion limit for a globular protein: 120,000, particle size: 44 to 105 μm, made by CHISSO CORPORATION) (hereinafter referred to as GC 200-m) as a porous cellulose gel, 4 g of 20% NaOH, 12 g of heptane and one drop of a nonion-type surfactant Tween 20 were added. After agitating for 2 hours at 40° C., 5 g of epichlorohydrin was added thereto and agitated for 2 hours at 40° C. Then, the obtained gel was washed with water and filtrated to obtain an epoxidated cellulose gel. The amount of the introduced epoxy group was 30 μmol per ml of the volume of the column. To 2 ml of the obtained gel, 0.12 g of sodium dextran sulfate of which the limiting viscosity number was 0.027 dl/g and the sulfur content was 17.7%, and 2 ml of water were added (the concentration of sodium dextran sulfate was approximately 2.5%). And, the obtained admixture was adjusted to pH 11 and shaked for 16 hours at 45° C. After that, the gel was filtered off and was washed with a 2M aqueous solution of sodium chloride, a 0.5M solution of sodium chloride and water in this turn to obtain the cellulose gel on which sodium dextran sulfate was immobilized (hereinafter referred to as G-1).

Preparation of human IL-8: *E. coli*-expressed recombinant human IL-8 (made by R & D systems) was prepared to have a predetermined concentration using phosphate-buffered saline (PBS) containing 0.1% BSA.

Adsorption operation: A PBS solution, which was prepared so as to contain 10 mg of GC 200-m or the above-mentioned G-1 as dry weight and 5 ng/ml human IL-8, was added to a polypropylene tube (made by Eppendorf) and the obtained admixture was shaked for 2 hours at 37° C.

Analyzing method: A part of supernatant of each sample was taken and the concentration of IL-8 was measured by means of a measurement kit for human IL-8 made by R & D systems. And, the adsorption ratio of IL-8 was calculated.

The results of the analysis are shown in TABLE 1.

TABLE 1

| Adsorbent | Adsorption ratio of human IL-8 |
|---|---|
| GC 200-m | 0% |
| G-1 | 98% |

EXAMPLE 2

The preparation of the adsorbent G-1 was carried out in the same way as in EXAMPLE 1.

The preparation of human IL-8 was carried out in the same way as in EXAMPLE 1.

Adsorption operation: A PBS solution, which was prepared so as to contain 10 mg of GC 200-m or G-1 obtained in the same way as in EXAMPLE 1 as dry weight, 50% human serum of a final volume and 5 ng/ml human IL-8, was added to a polypropylene tube (made by Eppendorf) and the obtained admixture was shaked for 2 hours at 37° C.

Analyzing method: Each sample was measured in the same way as in EXAMPLE 1.

The results of the analysis are shown in TABLE 2.

TABLE 2

| Adsorbent | Adsorption ratio of human IL-8 |
|---|---|
| GC 200-m | 0% |
| G-1 | 95% |

EXAMPLE 3

The preparation of the adsorbent G-1 was carried out in the same way as in EXAMPLE 1.

The preparation of human IL-8 was carried out in the same way as in EXAMPLE 1.

Adsorption operation: A PBS solution, which was prepared so as to contain 10 mg of GC 200-m or G-1 as dry weight, 70% human serum of a final volume and 5 ng/ml human IL-8, was added to a polypropylene tube (made by Eppendorf) and the obtained admixture was shaked for 2 hours at 37° C.

Analyzing method: Each sample was measured in the same way as in EXAMPLE 1.

The results of the analysis are shown in TABLE 3.

TABLE 3

| Adsorbent | Adsorption ratio of human IL-8 |
|---|---|
| GC 200-m | 0% |
| G-1 | 90% |

EXAMPLE 4

The preparation of the adsorbent G-1 was carried out in the same way as in EXAMPLE 1.

The preparation of human IL-8 was carried out in the same way as in EXAMPLE 1.

Adsorption and recovering operation: SEPACOL MINI PP which was a small column of polypropylene (made by SEIKAGAKU CORPORATION) was charged with 500 μl of a PBS suspension containing G-1 gel (dry weight was 30 mg), and 3 ml of a 5 ng/ml solution of human IL-8 containing 90% normal human serum was passed therethrough. The flow rate was controlled to approximately 0.1 ml/min by means of a peristaltic pump. Human IL-8 of the obtained effluent was measured in the same way as in EXAMPLE 1. Further, human IL-8 was then released and recovered with a PBS solution containing 0.5 M NaCl.

Analyzing method: Each sample was measured in the same way as in EXAMPLE 1.

The result of the analysis of the adsorption ratio is shown in TABLE 4. And, recovery ratio of human IL-8 was 98% (the adsorption amount was considered as 100%).

TABLE 4

| Adsorbent | Adsorption ratio of human IL-8 |
|---|---|
| G-1 | 94% |

EXAMPLE 5

Preparation of the adsorbent: Ten ml of GC 200-m was taken and dried by means of drying at a critical point in ethanol. The dried gel was suspended in 10 ml of a sufficiently dehydrated pyridine and was cooled with ice. Thereto, 2 ml of chlorosulfonic acid was added dropwise with agitating, and the agitation was continued for 10 minutes after the addition. After the reaction, the gel was filtrated and washed with pyridine and, then, with water to obtain a cellulose gel wherein an amount of sulfuric ester group to be 0.05 mmol/ml was introduced per unit volume (1 ml) (hereinafter referred to as G-2).

The preparation of human IL-8 was carried out in the same way as in EXAMPLE 1.

The adsorption and recovering operation was carried out in the same way as in EXAMPLE 4.

Analyzing method: Each sample was measured in the same way as in EXAMPLE 1.

The result of the analysis of adsorption ratio is shown in Table 5. And, the recovery ratio of human IL-8 was 98% (the adsorption amount was considered as 100%).

TABLE 5

| Adsorbent | Adsorption ratio of human IL-8 |
|---|---|
| G-2 | 91% |

EXAMPLE 6

Preparation of adsorbent: One hundred ml of cellulose beads CK-A3 (made by CHISSO CORPORATION, molecular weight of exclusion limit for a globular protein: $5 \times 10^6$, particle size: 45 to 105), 100 ml of water, 50 ml of 2M sodium hydroxide and 20 ml of epichlorohydrin were admixed in a reaction vessel, and reacted for 2 hours at 40° C. to obtain epoxidated cellulose beads CK-A3. In a reaction vessel, 100 ml of the obtained epoxidated cellulose beads CK-A3, 100 ml of water and 10 ml of 28% ammonia water were admixed and reacted over night at room temperature to obtain aminated cellulose beads CK-A3. On the other hand, 10 g of poly(sodium styrenesulfonate), 1 ml of thionyl chloride and 250 ml of toluene were admixed in a reaction vessel and reacted for 8 hours at room temperature to give partially chlorinated poly(sodium styrenesulfonate). In a reaction vessel, 10 g of the obtained chlorinated poly (sodium styrenesulfonate), 100 ml of the aminated cellulose beads CK-A3 and 100 ml of water were admixed and reacted over night to obtain poly(styrenesulfonic acid)-immobilized cellulose beads CK-A3.

Evaluation of adsorbent: The obtained poly (styrenesulfonic acid)-immobilized cellulose beads CK-A3 were equilibrated with physiological saline. These beads (0.5 ml) were introduced in a test tube, and excess physiological saline was removed. Thereto, 3 ml of human serum containing approximately 1.3 ng/ml of IL-1β or approximately 750 pg/ml of IL-2 was added and shaked for 2 hours at 37° C. Concentration of IL-1β or IL-2 in supernatant was measured by means of ELISA method.

The results of the analysis are shown in TABLE 6.

EXAMPLE 7

Preparation of adsorbent: To 100 ml of epoxidated cellulose beads CK-A3 obtained in the same way as in EXAMPLE 6, 6 g of sodium dextran sulfate, of which the limiting viscosity number was 0.27 dl/g and the sulfur content was 17.7%, and 100 ml of water were added (concentration of sodium dextran sulfate was approximately 2.5%) and adjusted to pH 11 and shaked for 16 hours at 45° C. After that, the obtained gel was filtered off and washed with water to obtain sodium dextran sulfate-immobilized cellulose beads CK-A3.

Evaluation of the adsorbent was carried out in the same way as in EXAMPLE 6 with respect to the sodium dextran sulfate-immobilized cellulose beads CK-A3.

The results of the analysis are shown in TABLE 6.

COMPARATIVE EXAMPLE 1

With respect to the cellulose beads CK-A3 used in EXAMPLE 6, evaluation of the above-mentioned beads was carried out in the same way as in EXAMPLE 6.

The results of the analysis are shown in TABLE 6.

TABLE 6

| No. of Ex. or Com. Ex. | Concentration of IL-1β in supernatant (ng/ml) | Concentration of IL-2 in supernatant (pg/ml) |
|---|---|---|
| Ex. 6 | 0.4 | 311 |
| Ex. 7 | 0.5 | 560 |
| Com. Ex. 1 | 1.1 | 700 |

It is found that, contrary to COMPARATIVE EXAMPLE 1, each concentration of IL-1β and IL-2 in supernatant in Examples 6 and 7 is decreased, and IL-1β and IL-2 in a body fluid can be efficiently adsorbed and removed using the adsorbent of the present invention.

EXAMPLE 8

Preparation of adsorbent: In the same way as in EXAMPLE 6, poly(styrenesulfonic acid)-immobilized cellulose CK-A3 was obtained.

Evaluation of adsorbent: The obtained poly (styrenesulfonic acid)-immobilized cellulose beads CK-A3 were equilibrated with physiological saline. The beads (0.5 ml) were introduced into a test tube and excess physiological saline was removed. Thereto, 3 ml of human serum containing approximately 420 pg/ml of IL-6 was added and shaked for 2 hours at 37° C. The concentration of IL-6 in supernatant was measured by means of ELISA method.

The results of the analysis are shown in TABLE 7.

EXAMPLE 9

Preparation of adsorbent: In the same way as in EXAMPLE 7, sodium dextran sulfate-immobilized cellulose beads CK-A3 were obtained.

Evaluation of the adsorbent was carried out in the same way as in EXAMPLE 8 with respect to the sodium dextran sulfate-immobilized cellulose beads CK-A3.

The results of the analysis are shown in TABLE 7.

COMPARATIVE EXAMPLE 2

With respect to the cellulose beads CK-A3 used in EXAMPLE 6, evaluation of the above-mentioned beads was carried out in the same way as in EXAMPLE 8.

The results of the analysis are shown in TABLE 7.

TABLE 7

|  | Concentration of IL-6 in supernatant (pg/ml) |
| --- | --- |
| Ex. 8 | 110 |
| Ex. 9 | 130 |
| Com. Ex. 2 | 330 |

It is found that, contrary to COMPARATIVE EXAMPLE 2, each concentration of IL-6 in supernatant in Examples 8 and 9 is decreased, and IL-6 in a body fluid can be efficiently adsorbed and removed using the adsorbent of the present invention.

INDUSTRIAL APPLICABILITY

Using the adsorbent comprising a water-insoluble carrier having an anionic functional group and an adsorber of the present invention, IL-8, IL-1β, IL-6 and/or IL-2 which can be pathogenic substances, can be efficiently adsorbed and removed and, if necessary, recovered from a body fluid of a patient, such as blood, plasma or serum.

We claim:

1. A method for adsorbing and removing at least one interleukin selected from the group consisting of interleukin-8, interleukin-1β, interleukin-6 and interleukin-2, comprising bringing an adsorbent into contact with a body fluid, wherein said adsorbent comprises a water-insoluble carrier having an anionic functional group for adsorbing at least one interleukin selected from the group consisting of interleukin-8, interleukin-1β, interleukin-6, and interleukin-2.

2. The method of claim 1, wherein the anionic functional group comprises at least one kind of group selected from the group consisting of sulfuric ester group, sulfonic acid group, carboxyl group and phosphoric ester group.

3. The method of claim 1, wherein the anionic functional group is originated from at least one moiety selected from the group consisting of sulfuric acid, dextran sulfate and poly(styrenesulfonic acid).

4. The method of claim 1, wherein the anionic functional group is a polyanionic functional group having plural anionic functional groups within said functional group.

5. The method of claim 1, which is characterized in that the water-insoluble carrier is hydrophilic.

6. The method of claim 1, which is characterized in that there exists an end functional group represented by —OH in the water-insoluble carrier.

7. The method of claim 1, which is characterized in that the water-soluble carrier is porous.

8. The method of claim 1, wherein the body fluid, after contacting the adsorbent, is returned to a body from which the body fluid was obtained.

9. A method for recovering at least one interleukin selected from the group consisting of interleukin-8, interleukin-1β, interleukin-6 and interleukin-2, which comprises a step to adsorb the interleukin by bringing a water-insoluble carrier having an anionic functional group into contact with body fluid which contains at least one interleukin selected from the group consisting of interleukin-8, interleukin-1β, interleukin-6 and interleukin-2 and a step to elute the adsorbed interleukin.

10. The method of claim 9, wherein the body fluid, after contacting the water-insoluble carrier having an anionic functional group, is returned to a body from which the body fluid was obtained.

* * * * *